(12) United States Patent
Armstrong et al.

(10) Patent No.: US 11,324,617 B2
(45) Date of Patent: May 10, 2022

(54) ENDOPROSTHESIS DELIVERY SYSTEMS WITH DEPLOYMENT AIDS

(71) Applicant: W. L. Gore & Associates, Inc., Newark, DE (US)

(72) Inventors: Joseph R. Armstrong, Flagstaff, AZ (US); Edward H. Cully, Flagstaff, AZ (US); Jeffrey B. Duncan, Flagstaff, AZ (US); Larry J. Kovach, Flagstaff, AZ (US); Douglas F. Pajot, Flagstaff, AZ (US); Brandon C. Short, Bellemont, AZ (US); Mark J. Ulm, Flagsaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 537 days.

(21) Appl. No.: 15/855,568

(22) Filed: Dec. 27, 2017

(65) Prior Publication Data
US 2018/0116842 A1    May 3, 2018

Related U.S. Application Data

(62) Division of application No. 14/198,037, filed on Mar. 5, 2014, now Pat. No. 9,855,160.
(Continued)

(51) Int. Cl.
*A61F 2/966* (2013.01)
*A61F 2/97* (2013.01)
*A61F 2/07* (2013.01)

(52) U.S. Cl.
CPC ............... *A61F 2/966* (2013.01); *A61F 2/07* (2013.01); *A61F 2/97* (2013.01); *A61F 2002/9665* (2013.01); *Y10T 29/49826* (2015.01)

(58) Field of Classification Search
CPC .. A61F 2/95; A61F 2/962; A61F 2/966; A61F 2/07; A61F 2/97; A61F 2002/9665;
(Continued)

(56) References Cited

U.S. PATENT DOCUMENTS 5,480,423 A * 1/1996 Ravenscroft ............. A61F 2/90
606/194
5,484,444 A    1/1996 Braunschweiler
(Continued)

FOREIGN PATENT DOCUMENTS

CN    1882293 A    12/2006
CN    2862980 Y    1/2007
(Continued)

OTHER PUBLICATIONS

International Search Report for PCT/US2014/021099 dated Jun. 23, 2014, corresponding to U.S. Appl. No. 14/198,037, 6 pages.

*Primary Examiner* — Tuan V Nguyen
*Assistant Examiner* — Chima U Igboko

(57) ABSTRACT

The present disclosure includes an endoprosthesis delivery system comprising an elongate member, such as a catheter, an endoprosthesis, a covering member disposed about the endoprosthesis, and at least one flexible element situated between the endoprosthesis and the covering member. The covering member can extend beyond an end of the endoprosthesis. In operation, as the covering member is removed, the flexible element can guide the covering member over the end of the endoprosthesis to prevent entanglement between the end of the endoprosthesis and the covering member.

17 Claims, 17 Drawing Sheets

Related U.S. Application Data

(60) Provisional application No. 61/782,134, filed on Mar. 14, 2013.

(58) Field of Classification Search
CPC ..... A61F 2002/9505; A61F 2002/9511; Y10T 29/49826
See application file for complete search history.

(56) References Cited

U.S. PATENT DOCUMENTS

| | | | |
|---|---|---|---|
| 6,077,295 A | 6/2000 | Limon | |
| 6,224,627 B1* | 5/2001 | Armstrong | A61F 2/82 623/1.13 |
| 6,302,893 B1 | 10/2001 | Limon | |
| 6,355,060 B1* | 3/2002 | Lenker | A61F 2/91 623/1.34 |
| 6,607,551 B1* | 8/2003 | Sullivan | A61F 2/95 623/1.11 |
| 7,198,636 B2 | 4/2007 | Cully et al. | |
| 7,556,641 B2 | 7/2009 | Cully | |
| 7,753,945 B2 | 7/2010 | Bruun | |
| 7,763,063 B2 | 7/2010 | Arbefeuille | |
| 7,771,463 B2 | 8/2010 | Ton | |
| 7,918,880 B2 | 4/2011 | Austin | |
| 8,591,566 B2 | 11/2013 | Newell | |
| 8,821,563 B2 | 9/2014 | Orr | |
| 9,095,463 B2 | 8/2015 | Argentine | |
| 2001/0001833 A1 | 5/2001 | Ravenscroft | |
| 2002/0016597 A1* | 2/2002 | Dwyer | A61F 2/95 606/108 |
| 2004/0267281 A1* | 12/2004 | Harari | A61F 2/966 606/108 |
| 2005/0049667 A1 | 3/2005 | Arbefeuille et al. | |
| 2006/0111771 A1 | 5/2006 | Ton | |
| 2006/0271149 A1 | 11/2006 | Berez | |
| 2007/0233224 A1* | 10/2007 | Leynov | A61F 2/95 623/1.12 |
| 2009/0030497 A1 | 1/2009 | Metcalf | |
| 2009/0198318 A1 | 8/2009 | Berez | |
| 2009/0276027 A1 | 11/2009 | Glynn | |
| 2011/0257720 A1 | 10/2011 | Peterson | |
| 2011/0301702 A1 | 12/2011 | Rust et al. | |
| 2012/0259403 A1 | 10/2012 | Hendriksen et al. | |
| 2013/0226278 A1* | 8/2013 | Newell | A61F 2/82 623/1.12 |

FOREIGN PATENT DOCUMENTS

| | | |
|---|---|---|
| CN | 101180006 A | 5/2008 |
| CN | 101299975 A | 11/2008 |
| DE | 102010050569 A1 | 5/2012 |
| EP | 0819411 A2 | 1/1998 |
| EP | 1929979 A2 | 6/2008 |
| JP | 10-057502 A | 3/1998 |
| JP | 2002-518086 A | 6/2002 |
| JP | 2003-500104 A | 1/2003 |
| JP | 2006-515786 A | 6/2006 |
| JP | 2008-155017 A | 7/2008 |
| JP | 2011-519608 A | 7/2011 |
| WO | WO-19980053761 A | 12/1998 |
| WO | 99/65420 A1 | 12/1999 |
| WO | 00/71058 A1 | 11/2000 |
| WO | 02/32496 A1 | 4/2002 |
| WO | 2004/066809 A2 | 8/2004 |
| WO | 2009/134801 A2 | 11/2009 |

* cited by examiner

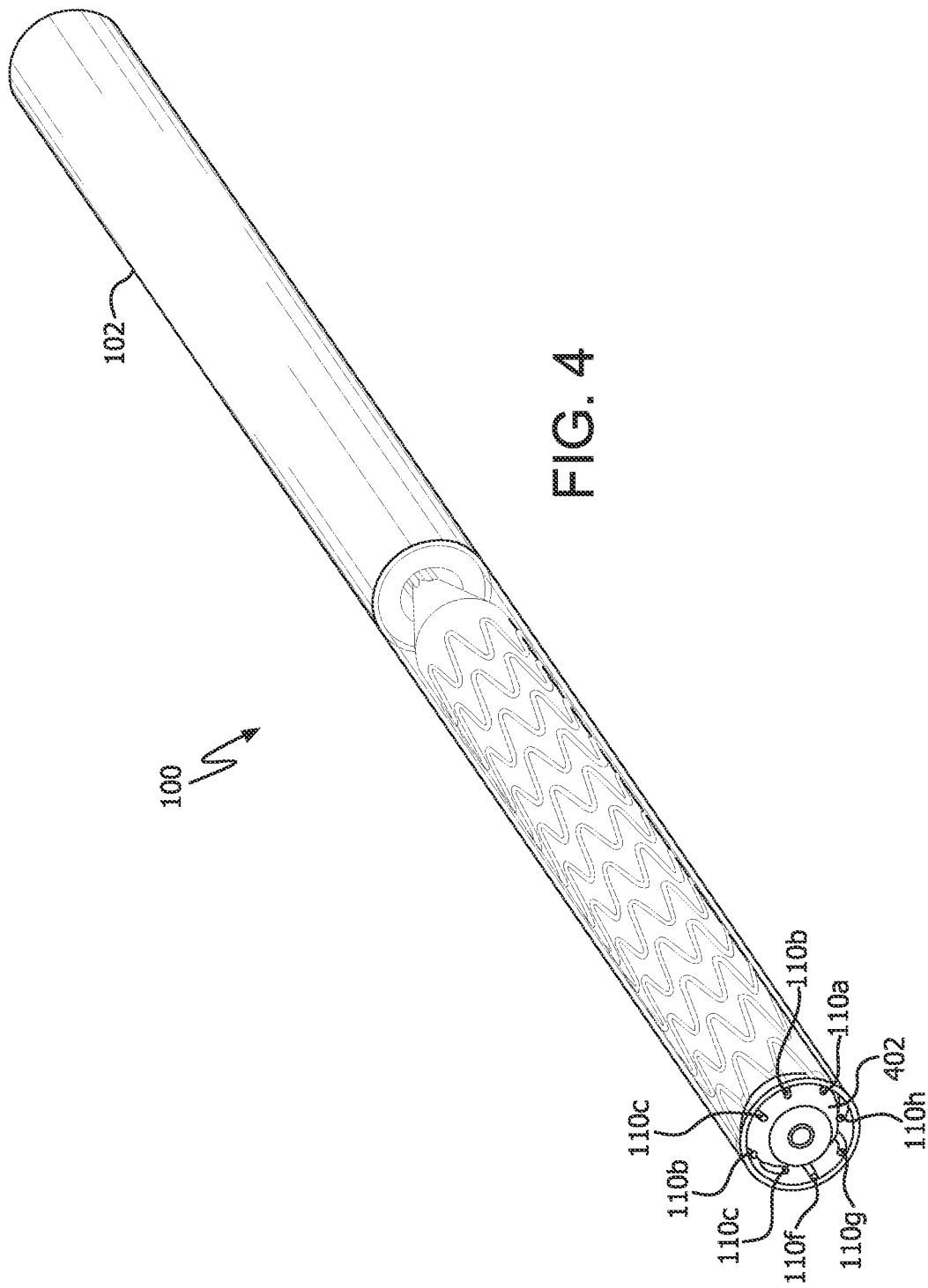

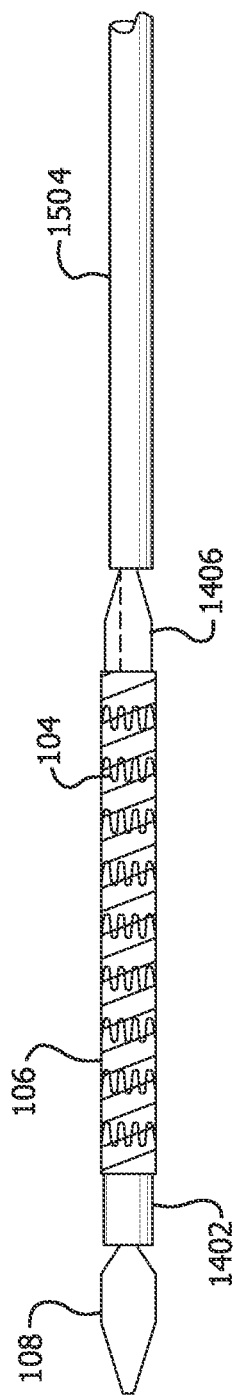
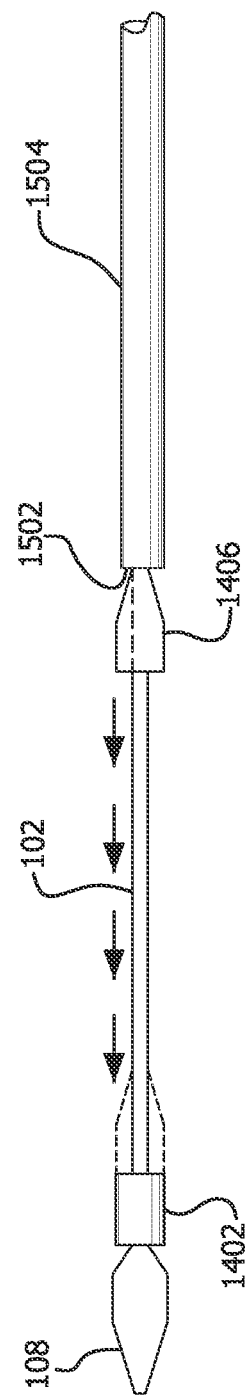

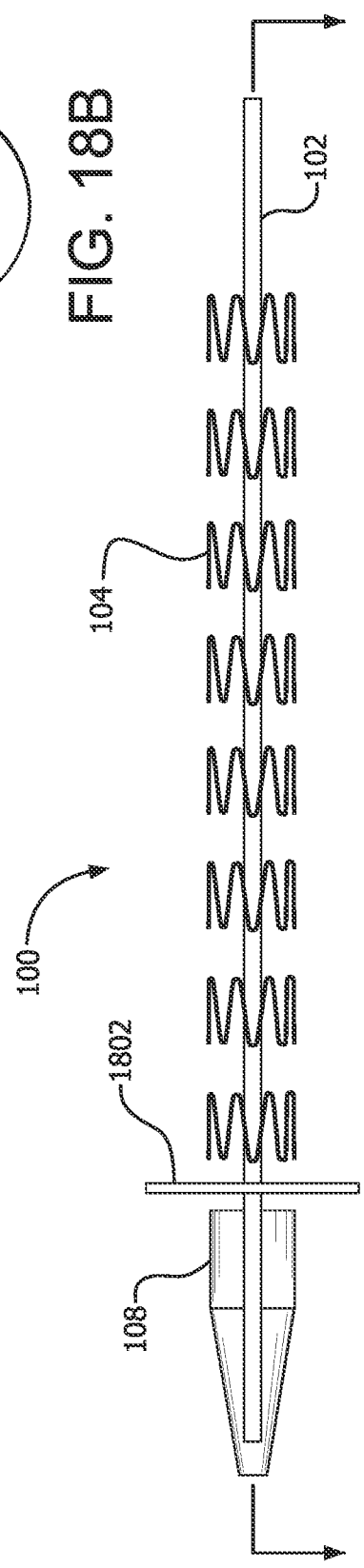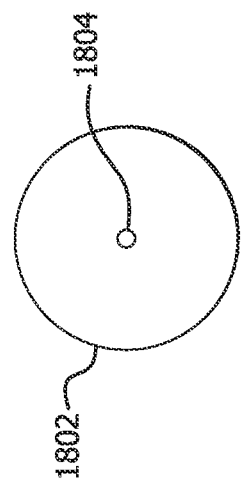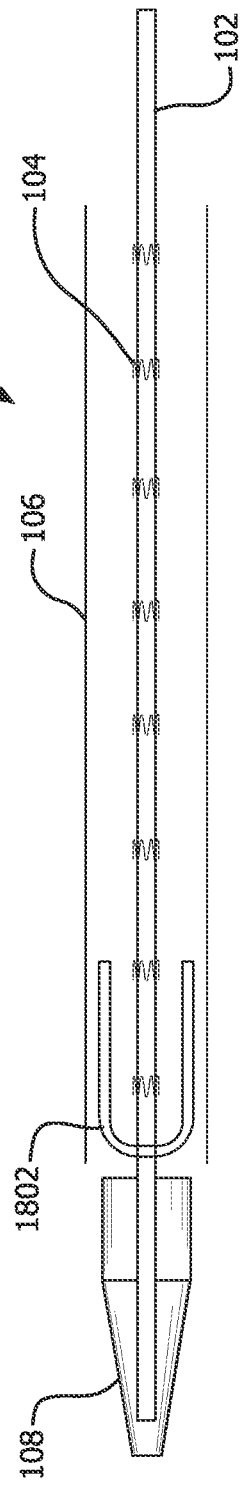

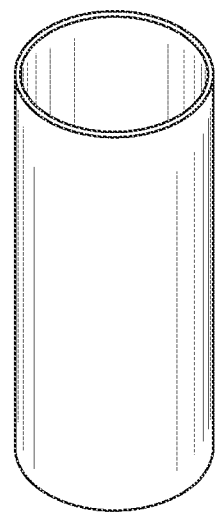
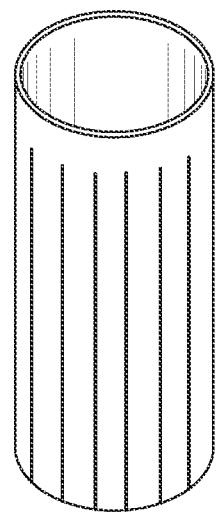
Film Tube · Slit Film Tube
FIG. 20A · FIG. 20B

ENDOPROSTHESIS DELIVERY SYSTEMS WITH DEPLOYMENT AIDS

CROSS-REFERENCE TO RELATED APPLICATION

This application is a divisional of U.S. patent application Ser. No. 14/198,037, filed Mar. 5, 2014, which claims priority to Provisional Application No. 61/782,134, filed Mar. 14, 2013, both of which are herein incorporated by reference in their entireties for all purposes.

FIELD

The present disclosure generally relates to endoprostheses for treating diseases of the vasculature and similar anatomies, and more particularly to endoprosthesis delivery systems for preventing entanglement of covering members with such endoprostheses.

BACKGROUND

Many endoprostheses (or endoprosthetic devices), such as, for example, stent-grafts, are constructed to reinforce, replace, bridge, or otherwise treat a part of a blood vessel. An endoprosthesis may thus guide blood flow through a lumen defined by a generally tubular interior of such a vessel. Other tubular endoprostheses are designed for use in other body regions, for example, the esophagus, ureters, gastrointestinal tract and various ducts. In many cases, endoprostheses are constrained within a covering member or sheath, and when the covering member is removed, as during deployment, the devices expand, are expanded under force or self-expand to assume a larger diameter. From time to time, however, as a covering member is removed, the member may snag, catch, or become entangled on the endoprosthesis. Thus, improved endoprosthesis delivery systems are desirable.

SUMMARY

The present disclosure includes an endoprosthesis delivery system comprising an elongate member, such as a catheter, an endoprosthesis, a covering member disposed about the endoprosthesis, and at least one flexible element situated between the endoprosthesis and the covering member. The covering member can extend beyond an end of the endoprosthesis. In operation, as the covering member is removed, the flexible element can guide the covering member over the end of the endoprosthesis to prevent entanglement between the end of the endoprosthesis and the covering member.

The present disclosure further includes an endoprosthesis delivery system comprising an elongate member having a slip resistant section or material, an endoprosthesis, and a covering member. The slip resistant material can comprise a gummy or mildly sticky material or a compressible material as described, and it can extend beyond a distal and/or proximal end of the endoprosthesis. In operation, as the covering member unravels or is otherwise removed to release the endoprosthesis, the slip resistant material can impede bunching of the cover. This can, in turn, prevent, or help to prevent, entanglement between the covering member and the endoprosthesis.

The present disclosure further includes an endoprosthesis delivery system comprising an elongate member, an endoprosthesis having a distal and/or proximal edge, an end cap adjacent to one of these edges, and a covering member. The covering member can extend beyond an end of the endoprosthesis and over a surface of the end cap. In operation, as the covering member is removed, the end cap can prevent the covering member from becoming entangled with an edge of the endoprosthesis. Rather, the covering member can follow the end cap as a guide over the edges of the endoprosthesis.

BRIEF DESCRIPTION OF THE DRAWINGS

The features and advantages of the present disclosure will become more apparent from the detailed description set forth below when taken in conjunction with the drawings, wherein:

FIG. 4 illustrates a cross-sectional view of an endoprosthesis delivery system taken along the line shown in FIG. 3;

FIG. 14 illustrates a perspective view an endoprosthesis delivery system having an end cap and a tapered end cap;

FIG. 15 illustrates a perspective view of an endoprosthesis delivery system in a post-deployment stage;

FIG. 18a illustrates a perspective view of an endoprosthesis delivery system prior to constraining an endoprosthesis in which a flexible element is fully opened;

FIG. 18b illustrates a shape of a flexible element when viewed axially;

FIG. 18c illustrates a constrained endoprosthesis with a flexible element placed between an endoprosthesis and an endoprosthesis covering element;

FIG. 20A illustrates a film tube capable of forming a portion of an endoprosthesis delivery system;

FIG. 20B illustrates a film tube including a plurality of slits for forming a portion of an endoprosthesis delivery system.

DETAILED DESCRIPTION OF THE ILLUSTRATED EMBODIMENTS

Figure 1:
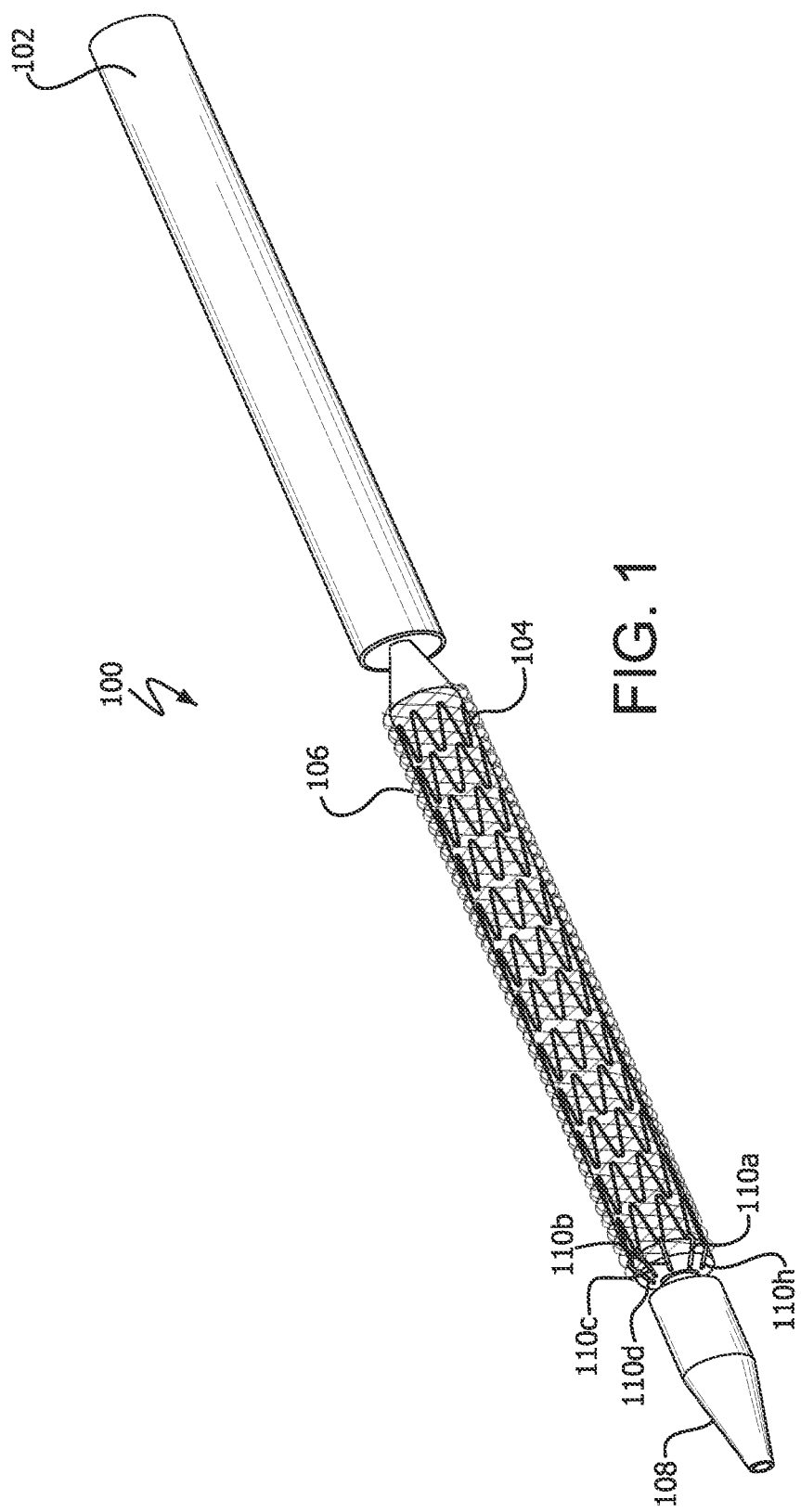
FIG. 1 illustrates a perspective view of an endoprosthesis delivery system.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The terms "endoprosthetic device," "endoprosthesis," "vascular device," and the like can refer, throughout the specification and in the claims, to any medical device capable of being implanted and/or deployed within a body lumen. In various embodiments, an endoprosthesis can comprise a stent, a stent-graft, graft, a filter, an occluder, a balloon, a lead, and energy transmission device, a deployable patch, an indwelling catheter, and the like.

In addition, throughout this specification and claims, the delivery systems described herein can, in general, include an endoprosthesis constrained by a "covering member" or "sheath." The covering member or sheath can, in various embodiments, comprise a sheet of material that is fitted about an endoprosthesis. The covering member or sheath can, in various embodiments, comprise a plurality of knitted fibers located about the endoprosthesis. These fibers can, for example, comprise a woven warp knit or knit-braid, as described in U.S. Pat. No. 6,315,792 to Armstrong et al., issued Nov. 13, 2001, entitled "Remotely removable covering and support," which is incorporated herein, in its entirety, by reference. The covering member can be coupled to a pull line extending down the length of the catheter, which a physician can pull to facilitate uncovering the endoprosthesis.

For example, a covering member comprising a plurality of fibers can be coupled to a pull line, which a physician can pull to unravel the plurality of fibers. Thus, the covering member can be characterized as "unzipping", in that the pull line causes the covering member to open or unzip along a straight line. In addition, in various embodiments, a covering member can be unzipped, first, along a proximal vector and, second, along a distal vector. In various embodiments, a covering member can be unzipped along a longitudinal vector running substantially parallel to the longitudinal axis of an elongate member.

Covering members can become caught on the endoprosthesis during deployment. For example, the covering member comprising a plurality of fibers can extend beyond an end or edge of an endoprosthesis, and as the covering member begins to be removed, e.g., unzipped, along a particular vector (e.g., a longitudinal vector), the member can become entangled with the end of the endoprosthesis. For example, the covering member can become entangled with one or more apices comprising the end of the endoprosthesis. Although the following description may often refer to a covering member comprising a plurality of fibers; in various embodiments, a covering member can comprise any of a variety of covers or sheaths capable of constraining an endoprosthesis.

As used throughout the specification and in the claims, the term "elongate member" can refer to a shaft-like structure such as a catheter, guidewire, introducer sheath, or the like. In various embodiments, an endoprosthesis can be mounted or loaded on a catheter, also referred to herein as an inner shaft, and, in a constrained diameter, fit within an introducer sheath, also referred to herein as an outer shaft.

Further, throughout this specification and in the claims, the term "distal" refers to a relative location that is farther from a location in the body at which the medical device was introduced. Similarly, the term "distally" refers to a direction away from a location in the body at which the medical device was introduced.

The term "proximal" refers, throughout the specification and in the claims, to a relative location that is closer to the location in the body at which the medical device was introduced. Similarly, the term "proximally" refers to a direction towards a location in the body at which the medical device was introduced.

With continuing regard to the terms proximal and distal, this disclosure should not be narrowly construed with respect to these terms. Rather, the devices and methods described herein may be altered and/or adjusted relative to the anatomy of a patient.

As used herein, the term "constrain" may mean (i) to limit expansion, occurring either through self-expansion or expansion assisted by a device, of the diameter of an expandable implant, or (ii) to cover or surround, but not otherwise restrain, an expandable implant (e.g., for storage or biocompatibility reasons and/or to provide protection to the expandable implant and/or the vasculature).

Accordingly, while specific embodiments are described in greater detail below, in general, the present disclosure will focus primarily upon endoprosthesis delivery systems and methods, and in particular, systems and methods for delivery of endoprostheses covered by a covering member combined with mechanisms that prevent snagging or entanglement between the covering member and the endoprosthesis.

In various embodiments, an endoprosthesis delivery system can comprise an elongate member, such as a catheter, an endoprosthesis, a covering member disposed about the endoprosthesis, and at least one flexible element situated between the endoprosthesis and the covering member. The covering member can extend beyond an end of the endoprosthesis. The endoprosthesis delivery system can further comprise a compressible material section of the elongate member extending at least beneath an end of the stent.

In operation, as the covering member unravels, the flexible element can guide the covering member over the end of the endoprosthesis to prevent a catch, snag, or entanglement between the end of the endoprosthesis and the covering member. For example, in an embodiment where the covering element comprises a plurality of fibers and is removed in a proximal direction, the flexible element can overlay a distal edge of the endoprosthesis, and as the covering member unravels, one or more fibers can ride over the flexible element. Similarly, in another embodiment where the covering member is removed in a distal direction, the flexible element can guide one or more fibers over a proximal edge of the endoprosthesis. Thus, the flexible element can prevent or reduce the likelihood of the covering member becoming caught on the endoprosthesis during deployment of the device. Optionally, the flexible element can extend through an opening at least partially defined by an edge, such as an apex, or an aperture formed in a graft member.

In the same or different embodiments, an endoprosthesis delivery system can comprise an elongate member, such as a catheter, having a slip resistant section or material, an endoprosthesis, and a covering member or sheath. The slip resistant material can comprise a gummy or sticky material, a compressible material, or a longitudinally compressed material (or various combinations thereof) that is located on a section of catheter adjacent a distal and/or proximal end of the endoprosthesis. The sheath, as above, can comprise a knitted plurality of fibers and can extend beyond the distal and/or proximal end of the endoprosthesis and be collocated with the slip resistant section.

During deployment, as the sheath unravels to release the endoprosthesis, the slip resistant material can impede bunching of the sheath fibers. This can, in turn, prevent, or help to prevent, a snag or entanglement between the sheath and the endoprosthesis. For example, the portion of the slip resistant material that extends beyond the distal and/or proximal end of the endoprosthesis can act as a mild adhesive between the sheath and the catheter, so that as the pull line coupled to the sheath is retracted (e.g., to initiate deployment), the sheath does not merely follow the motion of the pull line and slide down an otherwise relatively smooth surface of the catheter, bunching as it slides, to eventually become hung or entangled with an end of the endoprosthesis. Rather, the slip resistant material can releasably or mildly bind the sheath to the catheter, so that pulling of the pull line does not result in bunching that could lead to a failed deployment. In various embodiments wherein the sheath comprises a plurality of fibers, the fibers can partially embed into the slip resistant material as the pull line is pulled.

In different or the same embodiments, an endoprosthesis delivery system can comprise an elongate member, for example a catheter, an endoprosthesis having a distal and/or proximal edge, an end cap adjacent to one of these edges, and a covering member, such as a knitted covering member as described above. The covering member can extend beyond an end of the endoprosthesis and over a surface of the end cap.

By way of example, in operation, as the covering member comprising a plurality of fibers unravels to uncover or release the endoprosthesis from a delivery and/or constrained diameter, the end cap can prevent the fibers from becoming hung or entangled with an edge of the endoprosthesis. Rather, the covering member can follow the end cap surface guiding it over the edges of the endoprosthesis.

Figure 2:
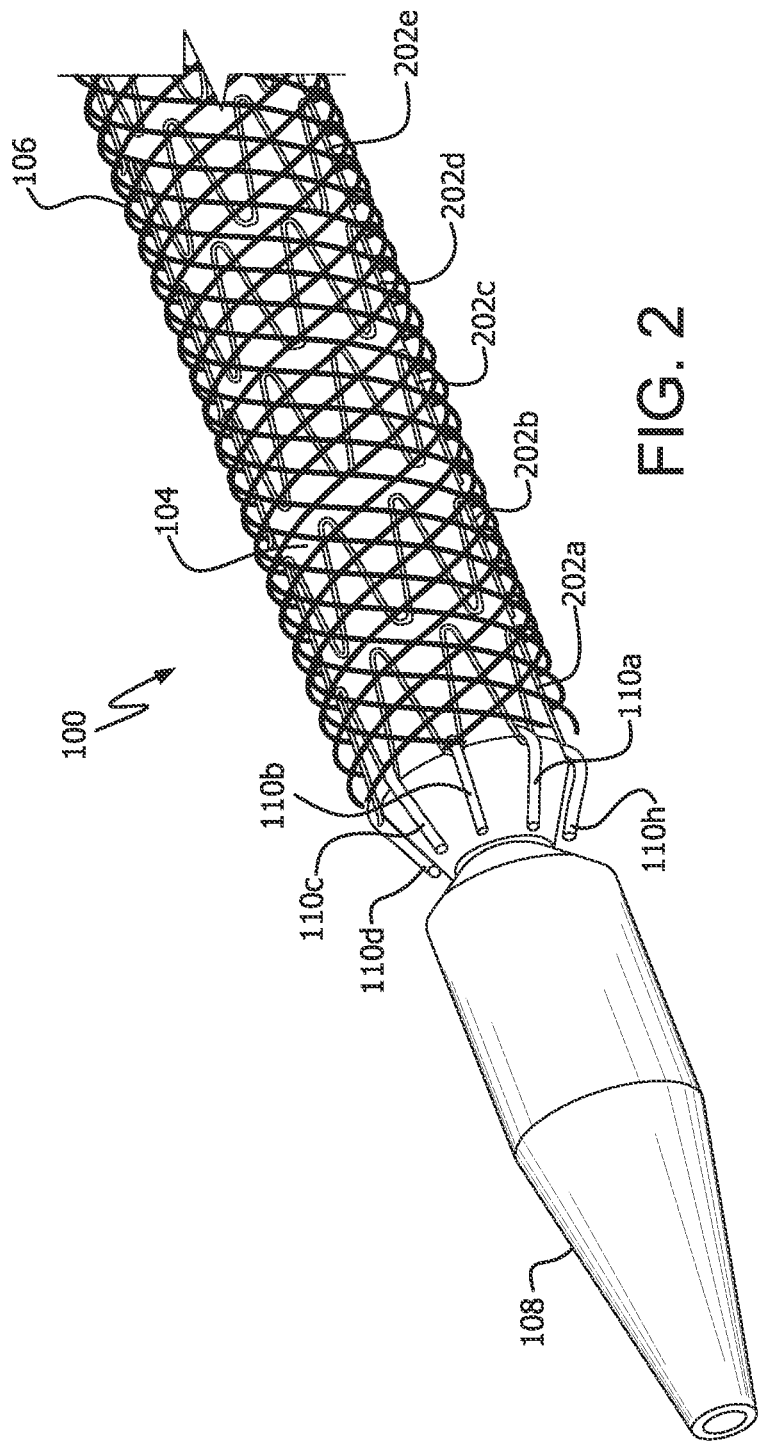
FIG. 2 illustrates a magnified perspective view of an endoprosthesis delivery system.
Figure 3:
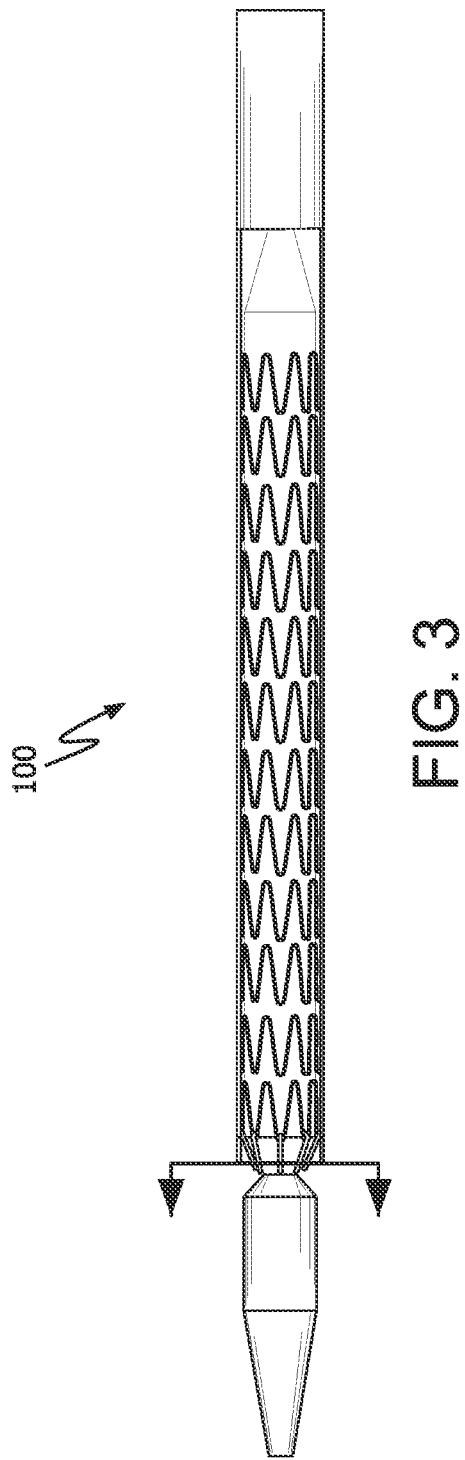
FIG. 3 illustrates a perspective view of an endoprosthesis delivery system, including a line along which a cross-sectional view is to be taken.

Now, as shown with reference to FIG. 1, and more closely with reference to FIG. 2, an endoprosthesis delivery system 100 can comprise, in various embodiments, an elongate member 102, an endoprosthesis 104, a covering member 106, and/or a catheter tip or "olive" 108. Further, as shown with reference to FIGS. 1-4 (and most clearly with reference to FIG. 4, which as shown at FIG. 3, illustrates a cross-sectional view of the delivery system 100), a delivery system 100 can comprise one or more flexible elements 110*a*-110*h*. In various embodiments, the distal edge of the covering member 106 can extend to a location just proximal of the ends of the flexible elements 110*a*-110*h*, for example, between the ends of elements 202*a*-202*e* (described below) and the distal ends of flexible elements 110*a*-110*h*. In certain embodiments, for example where covering member 106 comprises a plurality of woven warp knit or knit-braid fibers, the distal and/or proximal end regions of covering member 106 can be longitudinally compressed against the end(s) of endoprosthesis 104. This helps to reduce variability of such compression which might otherwise occur to a more random extent when the endoprosthesis delivery system 100 is passed through a hemostasis valve and/or when covering member 106 is deployed via a pull line.

Referring now mainly to FIG. 2, each of the flexible elements 110*a*-110*h* can extend over, or overlap or overlay, a distal edge of the endoprosthesis 104. For example, the endoprosthesis 104 can comprise a stent or stent graft, which can, in either case, include one or more stent elements 202*a*-202*e*, e.g., stent rings or windings. Each element 202*a*-202*e* can comprise a plurality of apices, and, with regard to a stent element located at a distal end (or a proximal end, in certain embodiments) of the endoprosthesis 104, such as stent element 202*a*, the flexible elements 110*a*-110*h* can overlap the apices formed in the stent element 202*a*. Similarly, where the endoprosthesis 104 comprises a stent graft, the flexible elements 110*a*-110*h* can overlay the distal edge, e.g., an apex, and optionally extend through the graft material by way of one or more openings formed (e.g., via a laser cutting tool) in the graft material.

While the figures show eight flexible elements, in various embodiments, the number of flexible elements can correspond to a number of apices associated with an endoprosthesis 104. Thus, there can be fewer or greater than eight flexible elements 110*a*-110*h*. Moreover, two or more flexible elements can overlay a single apex.

Figure 21:
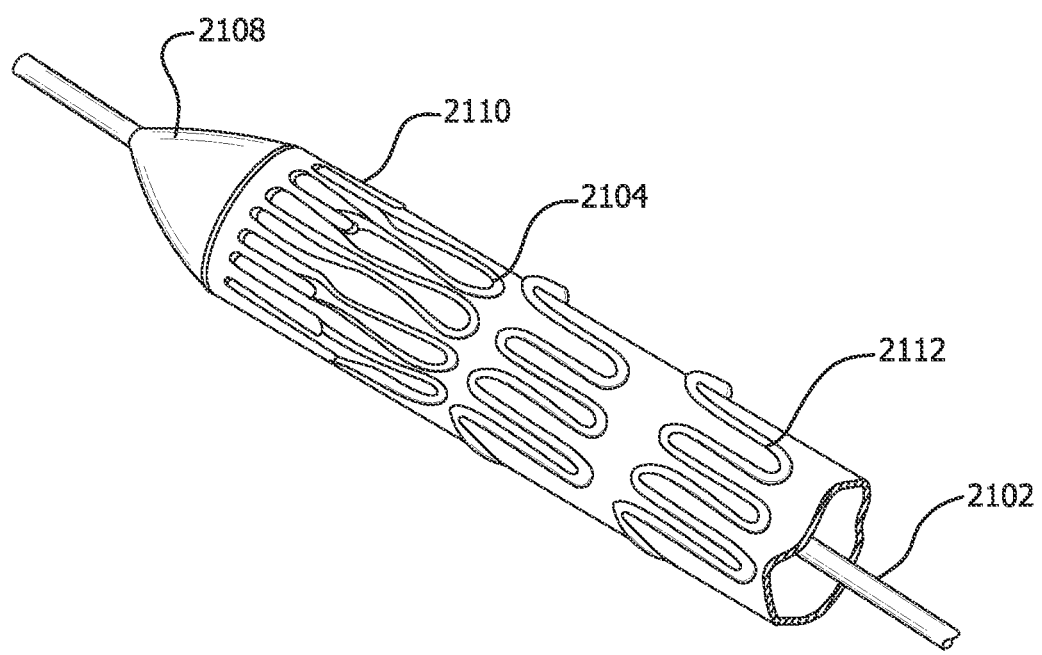
FIG. 21 illustrates an endoprosthesis delivery system.

In various embodiments, and with reference to FIGS. 20A and 20B, a flexible element 110*a*-110*h* can be formed by cutting or incising a film tube to create a plurality of slits within the film tube. A film tube having a plurality of slits is shown with respect to FIG. 20B, and as shown, the region between each slit can comprise one of the plurality of flexible elements 110*a*-110*h*. Similarly, as shown in FIG. 21, in other embodiments, the flexible element(s) 2110 formed from a film tube having a plurality of longitudinal slits shown in FIG. 20B can be secured to the distal region of the elongate member 2102, distal to the distal edge of the endoprosthesis 2104. For example, one or more flexible elements 2110 can be secured to a catheter olive 2108, or be positioned proximal thereto and extend proximally to overlay the edge of the endoprosthesis 2104, and optionally extend through openings formed adjacent to apices of the stent elements 2212.

As shown with respect to FIG. 4, the endoprosthesis delivery system 100 can further comprise a material 402 compressible in the z-axis, e.g., a material that comprises some loft or a soft material, such as a silicone, ePTFE, or polyurethane foam. The "z-axis" can refer to the axis which extends through the thickness of the material. The compressible material 402 can surround the elongate member 102. The z-axis compressible material 402 extends on a section of the elongate member, wherein the section is collocated at an edge of the endoprosthesis 104 and extends at least a small distance distally and/or proximally so that the edge of the tubular endoprosthesis, whether a proximal and/or distal edge, can at least partially embed itself into the compressible material 402. This can serve to prevent the covering member becoming entangled with the endoprosthesis from the underside thereof.

As such, the compressible material 402 can comprise any material in which an endoprosthesis 104 can be at least partially embedded when in a delivery configuration. For example, the compressible material 402 can be capable of compressing and/or densifying in response to the application of a radially compressive force, as described above. In various embodiments, the compressible material 402 can comprise any of the following and/or any combination of the following substances: silicones, polyurethane, polytetrafluoroethylene (PTFE), porous polymers, such as expanded polytetrafluoroethylene ("ePTFE"), fluorinated ethylene propylene (FEP), various foams, any polymeric material, any fluoropolymer based material, and the like. The compressible material may be in the form of a balloon, of complaint, semi-compliant, or non-compliant type. When slightly inflated, the balloon will serve the function of the compliant material. In addition, a balloon that is slightly longer than the endoprosthesis 104 can form one or more compliant olives at one or both ends of the endoprosthesis 104. Further, in various embodiments, a covering member 106 can be used to adjust the length of a balloon at the end of the endoprosthesis 104.

In various embodiments, the flexible element(s) 110 can comprise a compliant member. The compliant member can be sufficiently compliant to conform to a distal edge profile of an endoprosthesis. The flexible element(s) 110 can further be a slender, elongated member. For example, flexible element(s) 110 can comprise a filament or thread. The flexible element(s) can possess any variety of cross-sections, e.g., a circular, oval, square, elliptical, rectangular, polygonal, generally flat, or any variety of cross-sections. Moreover, in various embodiments, the flexible elements 110 can comprise a tube, tube like structure, or sock. The flexible element(s) can be manufactured by methods typically used to make fibers and the like and by injection molding, extrusion, and/or calendaring.

Figure 5:
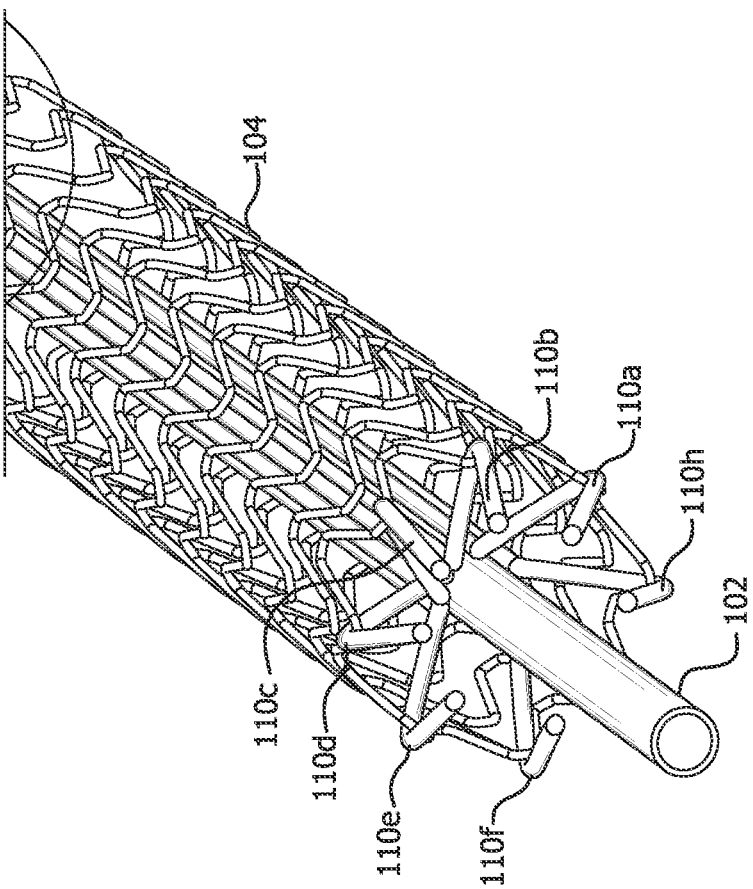
FIG. 5 illustrates a perspective view of an endoprosthesis delivery system without a compressible material.

A flexible element is secured to the elongate member 102. For example, a flexible element 110 can be coupled to elongate member 102 at a location proximal to the distal edge and extend through an opening to overlay the distal edge, as shown with reference to FIG. 5. The flexible element in this example is of an appropriate length so that the free end (the end not secured to the elongate member 102) is drawn out of the opening in an apex formed in the stent ring or winding as the endoprosthesis 104 deploys.

Figure 6:
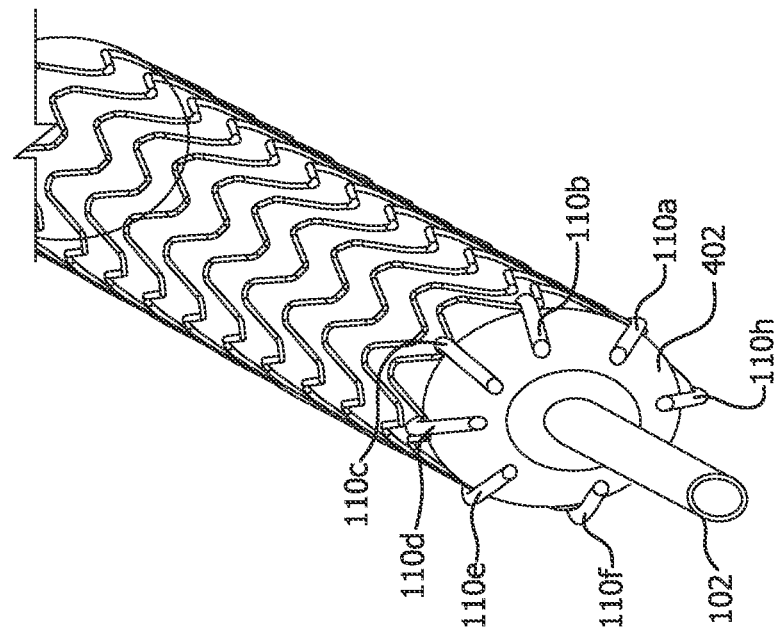
FIG. 6 illustrates a perspective view of an endoprosthesis delivery system with a compressible material.
Figure 7:
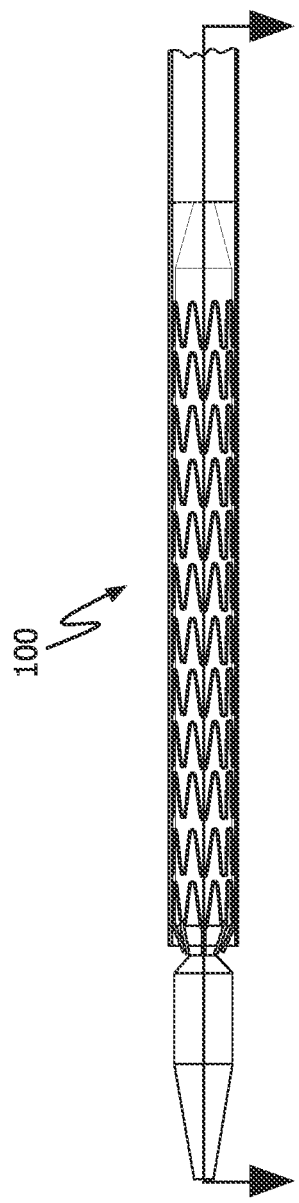
FIG. 7 illustrates a perspective view of an endoprosthesis delivery system, including a line along which a cross-sectional view is to be taken.
Figure 8:
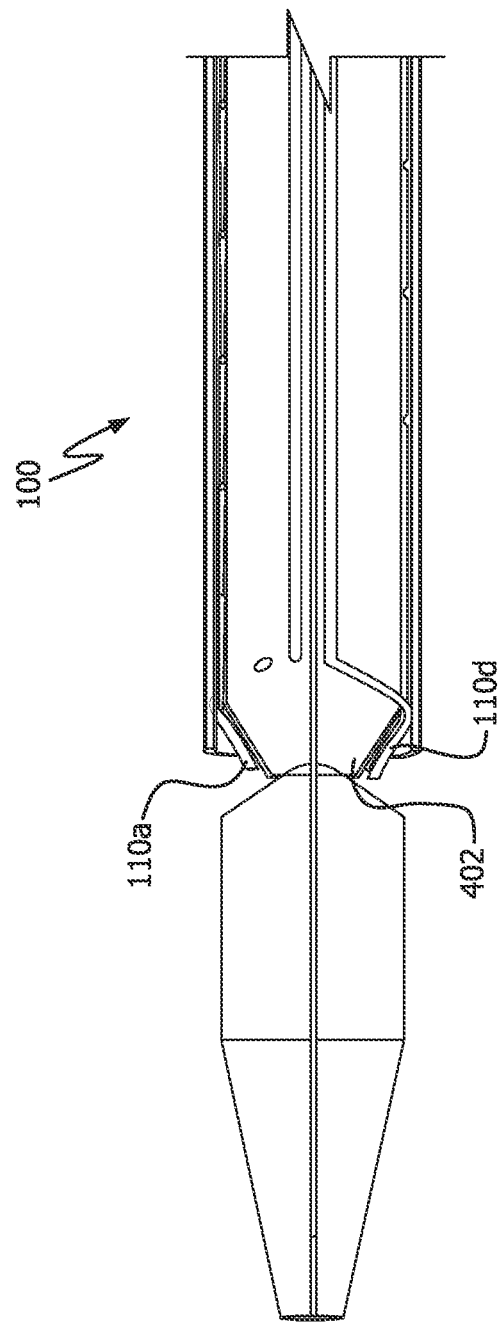
FIG. 8 illustrates a cross-sectional view of an endoprosthesis delivery system taken along the line shown in FIG. 7.
Figure 9:
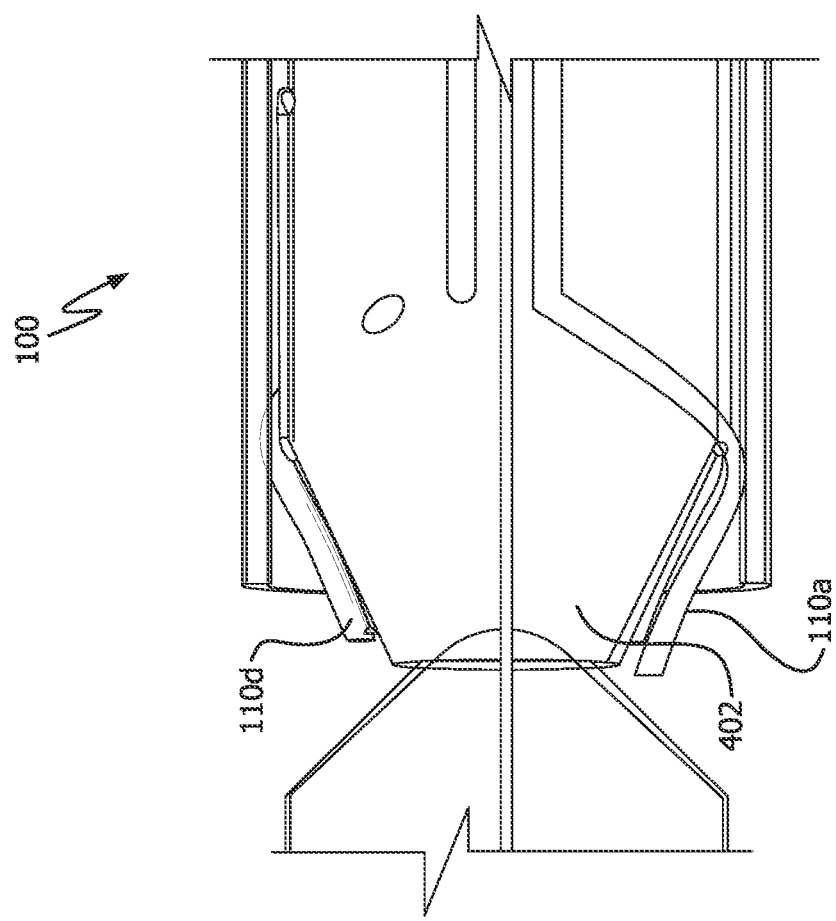
FIG. 9 illustrates a magnified and cropped cross-sectional view of an endoprosthesis delivery system taken along the line shown in FIG. 7.

In order to secure the flexible element, as shown with respect to FIG. 6, each flexible element 110a-110h can optionally extend into or beneath the compressible material 402. The flexible elements 110a-110h can, in this manner, be secured to the elongate member as each element extends proximally there under. This feature is illustrated in additional detail with respect to FIGS. 7-9. In particular, FIGS. 8 and 9 show cross-sectional views, taken along the line shown in FIG. 7, of an endoprosthesis delivery system 100. In these Figures, several flexible elements 110a and 110d can be seen overlapping their respective apices and extending in a proximal direction underneath the surface of the compressible material 402.

As shown in FIGS. 18A-18C, in other embodiments, the flexible element 110 can be formed as a thin, flexible disc 1802 which when attached to a catheter olive 108 or when positioned just proximal thereto as shown can be everted toward the endoprosthesis 104 to cover at least a portion of its edge. FIG. 18A shows the delivery system 100 with a distal olive 108, elongate member 102 and endoprosthesis 104 all in an unconstrained state, e.g., before a covering member 106 is applied. A front view of disc 1802, having a center hole 1804 for fitting with elongate member 102 is shown in FIG. 18B. Disc 1802 is shown in FIG. 18C as having been everted over the distal edge of endoprosthesis 104 and covering member 106 applied to constrain both endoprosthesis 104 and disc 1802. Upon removal of covering member 106, disc 1802 prevents covering member 106 from becoming caught on the distal edge of endoprosthesis 104 and as endoprosthesis 104 expands, the edges of disc 1802 are rotated outward. Disc 1802 can be made of any sufficiently flexible material, e.g., an elastomer such as silicone or thin sheet of a polymer such as ePTFE, so that the readily rotates away from the endoprosthesis 104. Disc 1802 can be made of different shapes of any sufficiently flexible material, e.g. a sheet, tube of circular cross section or other non uniform cross sections.

In further embodiments, disc 1802 may be provided with longitudinal weak zones or perforations which fracture upon expansion of endoprosthesis 104. In other embodiments, disc 1802 may feature a series of longitudinal cuts made around its circumference extending radially toward, but not extending to, the center hole 1804. Such cuts form a plurality of strands about at least a part of the disc's circumference. These strands can then be everted over the distal end of endoprosthesis 104 and serve to prevent covering member 106 from entangling with the distal edge thereof upon its removal.

At the point of attachment, flexible element can easily pivot or bend at its base, i.e., the point of catheter attachment, facilitating the flexible element sweeping through a wide range of motion. For example, the flexible element is capable of sweeping through at least a 90 degree arc along the longitudinal axis, at least a 180 degree arc along the longitudinal axis, at least a hemispherical range, or more.

Figure 10:
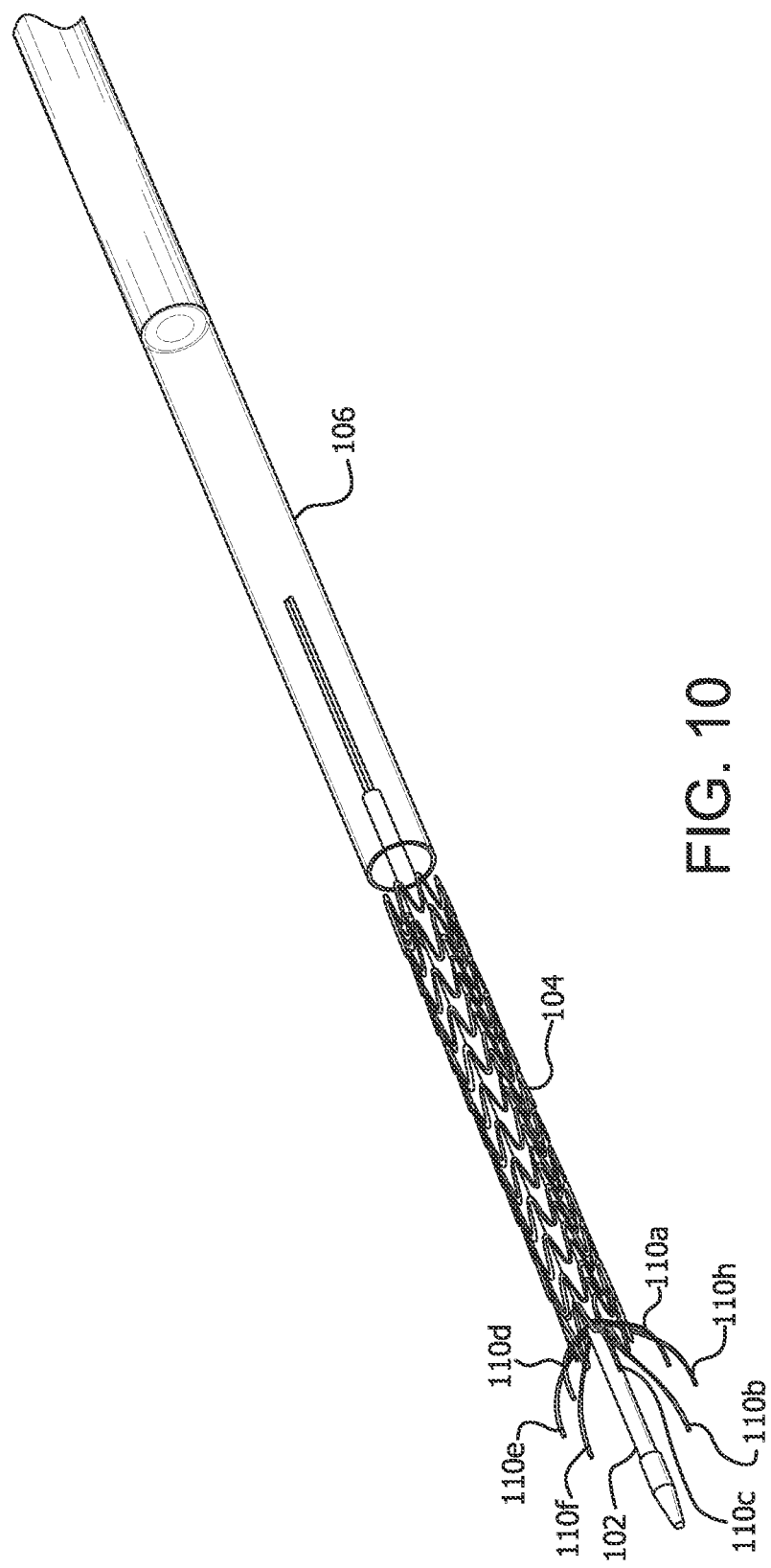
FIG. 10 illustrates a perspective view of an endoprosthesis delivery system in the process of deploying an endoprosthesis.
Figure 11:
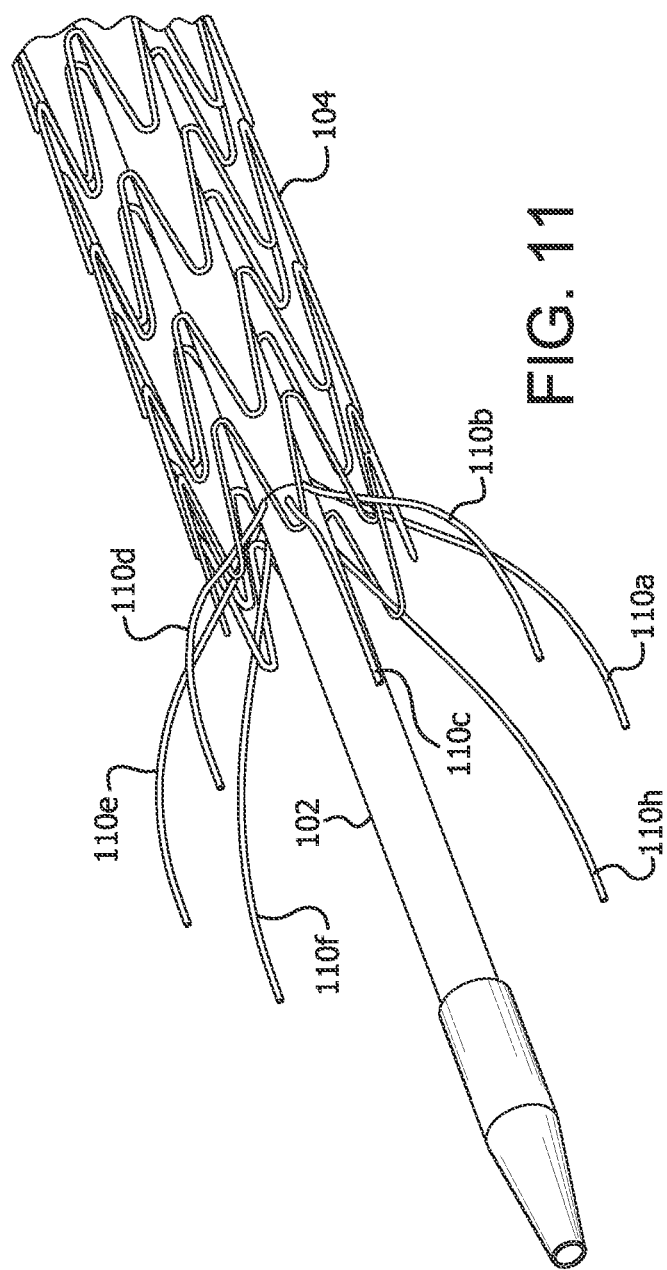
FIG. 11 illustrates a magnified perspective view of an endoprosthesis delivery system in the process of deploying an endoprosthesis.

With reference now to FIGS. 10 and 11, an endoprosthesis 104 can be delivered as shown. The covering member 106 can be unstitched, unzipped, unraveled, drawn away, or otherwise removed, as described herein, from the endoprosthesis 104. Covering member 106 is shown as being fully retracted for clarity but it will be understood that endoprosthesis 104 can progressively expand during gradual or stepwise withdrawal of covering member 106. As the covering member 106 is removed from an end of the endoprosthesis 104 (e.g., as depicted, from a distal end or region of the endoprosthesis 104), the flexible elements 110a-110h guide the retracting covering member 106 over the distal edge, e.g., at the apices, at the distal (or proximal, in other configurations) end of the endoprosthesis 104. As the covering member 106 uncovers the tubular endoprosthesis, the flexible elements 110a-110h can be pushed outward by the expanding endoprosthesis, and optionally retracted from an opening. This feature can be of particular help where, for example and as described above, the covering member 106 is of a braided or knitted structure, such a structure having openings capable of becoming entangled snagging, or catching on one or more apices as the covering member 106 is made to unzip through the proximal motion of a pull line coupled to the member 106.

Figure 12A:
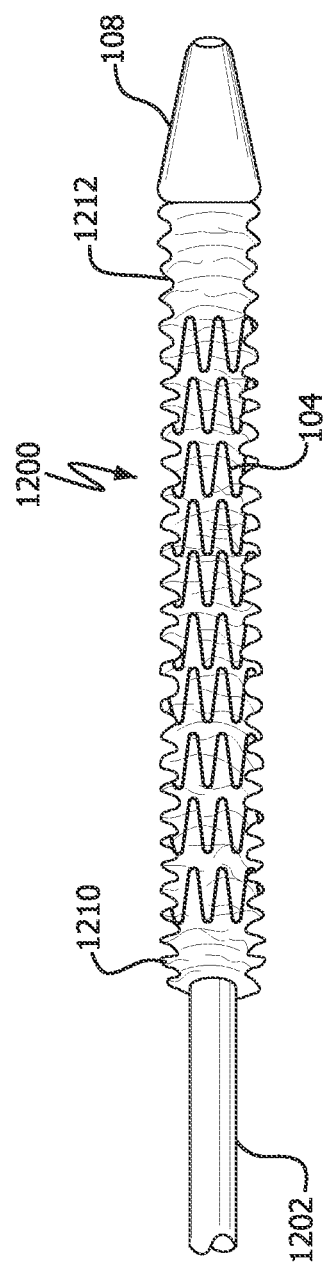
FIG. 12A illustrates perspective view of an endoprosthesis delivery system including a slip resistant material.

In various embodiments, and referring to FIG. 12A, an endoprosthesis delivery system 1200 can include an elongate member, an endoprosthesis 104, a covering member, as described above, and a slip resistant portion or material 1210 located about a section of catheter adjacent the endoprosthesis 104.

Figure 12B:
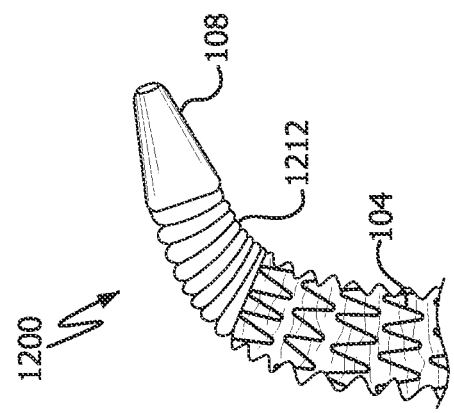
FIG. 12B illustrates a perspective view of an endoprosthesis delivery system including a flexible, longitudinally compressed polymeric member.

In various embodiments, the slip resistant material 1210 can be located on the elongate member 1202 adjacent to and/or underneath the endoprosthesis. As shown in FIG. 12 A, slip resistant material 1210 is positioned proximal of the olive 108, extending under endoprosthesis 104 and terminating proximal thereto. In various embodiments, slip resistant material may extend a longer or shorter distance, e.g., it may extend proximal of the olive 108 to just under the distal edge of endoprosthesis 104 or abut the distal edge of the endoprosthesis.

In various embodiments, the slip resistant material 1210 can comprise a z-axis compressible material, as described above. In same or different embodiments, the slip resistant material 1210 can be longitudinally compressed, as shown, so that its surface is not smooth, but wrinkled or ribbed, giving it a more "abrasive" surface to resist bunching of the covering member. Further, in same or different embodiments, the slip resistant material 1210 can be gummy or mildly sticky or adhesive. Slip resistant material can be made of a variety of materials such as adhesives, materials coated with adhesives, spongy materials possessing loft, foams, or materials that are compressible. One such material can be made of a polymer such as PTFE or an ePTFE. In certain embodiments, slip resistant material 1210 may be incorporated with or serve as the olive 108. In such embodiments, the distal end of the endoprosthesis 104 will extend over at least a portion of the olive 108. Where slip resistant material 1210 forms the olive 108, said material can comprise a foam.

Figure 19:
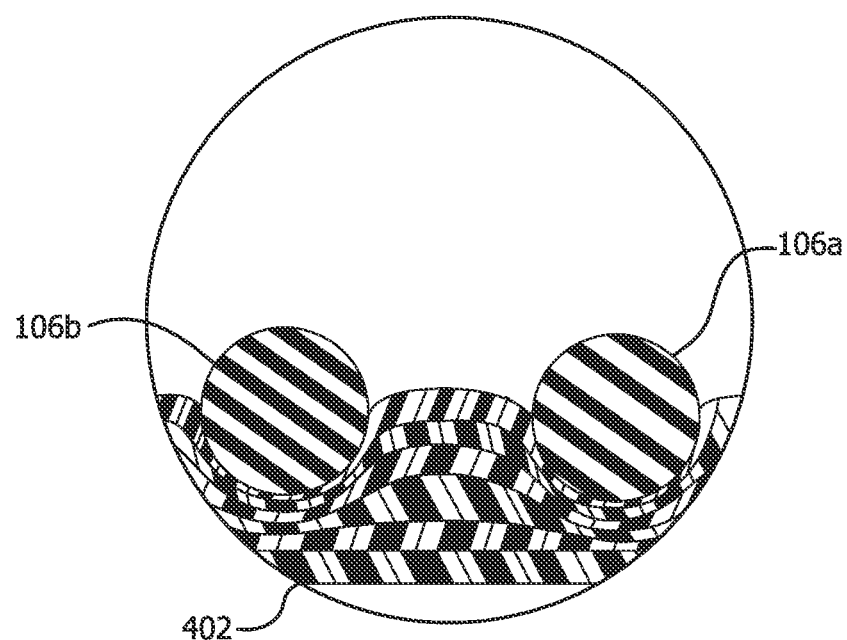
FIG. 19 illustrates a cross-sectional view of an endoprosthesis delivery system.

During deployment, the covering member (not shown) can be removed, e.g., by unraveling or unzipping, to release the endoprosthesis 104 from a constrained configuration. In various embodiments, as the covering member unzips, the covering member can stick to and/or at least partially embed into the slip resistant material 1210, for example in a distal portion or segment 1212 of the slip resistant material 1210, so that the covering member is impeded from bunching as a pull line coupled to the covering member is pulled to deploy or uncover the endoprosthesis. A cross-sectional illustration of a covering member embedded within a slip resistant or otherwise compressible material is shown at FIG. 19. With reference to FIG. 19, as shown, one or more sheath or covering member fibers 106a and/or 106b can be embedded within a compressible material 402. This can, in turn, prevent, or help to prevent a snag or entanglement between the covering member and the endoprosthesis 104. In various embodiments, slip resistant material 1210, in particular segment 1212, can function to elongate along the outer radius when bent and thus minimizing a gap formed between the proximal face of olive 108 and the distal edge of the endoprosthesis 104. If the covering member extends proximally or over olive 108, segment 1212 will prevent covering member from slipping into said gap. If this occurs, covering member has an increased likelihood of becoming caught on the endoprosthesis 104.

With particular attention to the interface between the edge of the endoprosthesis 104 and the covering member, as the pull line coupled to the covering member is retracted, the covering member, as it is removed proximally, can be impeded by its bond with the segment 1212 of slip resistant material 1210 from sliding down what might otherwise comprise a relatively smooth surface of the elongate member, bunching in the process, to eventually become entangled with an end of the endoprosthesis 104. Thus, the segment 1212 of slip-resistant material 1210 can prevent or reduce entanglement of the covering member with an end of the endoprosthesis 104.

In addition, in a further embodiment, the segment 1212 of slip resistant material 1210 can extend underneath the edge of the endoprosthesis, and the edge of endoprosthesis can be at least partially embedded into the segment 1212 of slip-resistant material 1210. For example, one or more apices at the edge of the endoprosthesis 104 can be embedded into or nested within the folds of the slip resistant material. Therefore, as the covering member is removed, the member can simply ride over the end of the endoprosthesis 104, and this can further reduce entanglement between the end of the endoprosthesis 104 and the covering member. Further still, in certain embodiments, the segment 1212 of the slip resistant material 1210 can act to share the load with the endoprosthesis 104. For example, as the endoprosthesis is maneuvered through the anatomy of a patient (particularly, tortuous anatomy), the segment 1212 of slip resistant material 1210 can permit the endoprosthesis delivery system 1200 to navigate through the anatomy more gently, e.g., by turning around curves and corners more subtly and/or gently.

Figure 13A:
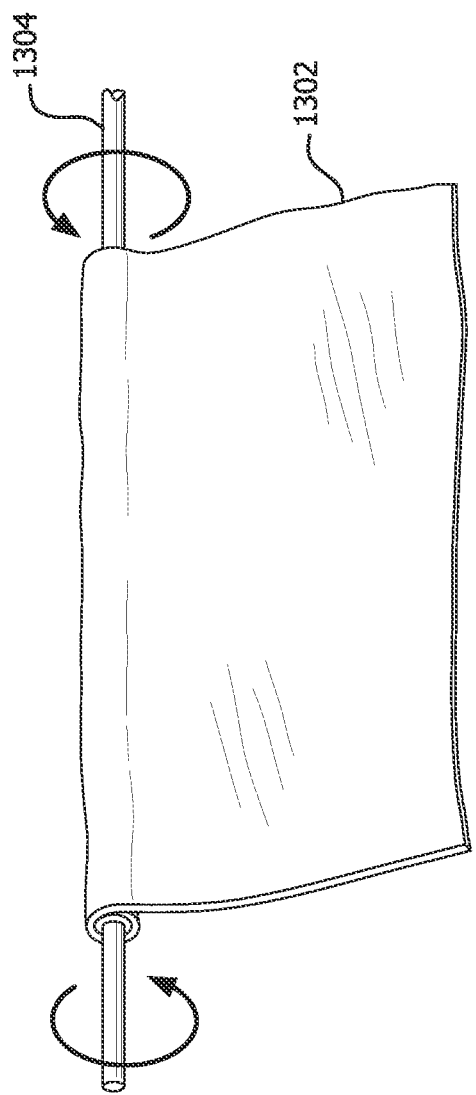
FIG. 13A illustrates a perspective view of a method of manufacturing an endoprosthesis delivery system comprising rolling a sheet of compliant material about a mandrel.
Figure 13B:
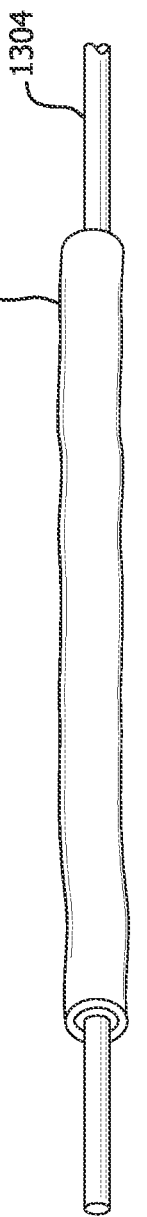
FIG. 13B illustrates a perspective view of a method of manufacturing an endoprosthesis delivery system comprising curing a rolled sheet of compliant material.
Figure 13C:
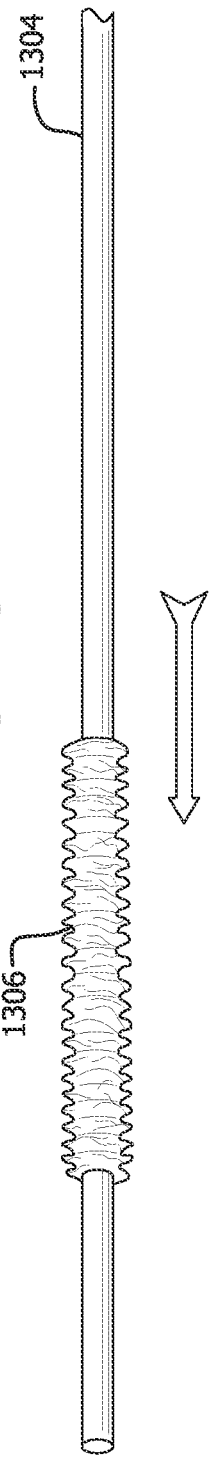
FIG. 13C illustrates a perspective view of a method of manufacturing an endoprosthesis delivery system comprising longitudinally compressing a rolled sheet of compliant material to form a slip resistant material.

A slip resistant material 1210 can be manufactured, in various embodiments, as shown at FIGS. 13A-13C. In particular, as shown at FIG. 13A, a sheet or tape of compliant material 1302 can be wound or rolled about a mandrel 1304. In various embodiments, compliant material 1302 can comprise a sheet or tape of thin flexible polymeric sheet and optionally, a porous polymer, such as an ePTFE membrane. Now, as shown with reference to FIG. 13B, the rolled sheet 1306 can be treated, e.g., thermally treated, to prevent it from unrolling and/or adhere it together. Alternatively or in addition thereto, the rolled sheet can be cured with a flexible and optionally an elastomeric adhesive, such as a thermoplastic copolymer of tetrafluoroethylene and perfluoroalkylvinylether as described in U.S. Pat. No. 8,048,440 entitled "Thermoplastic Fluoropolymer-Coated Medical Devices" and U.S. Pat. No. 7,462,675 entitled "Thermoplastic Copolymer of tetrafluoroethylene and perfluoromethyl vinyl ether and Medical Devices Employing the Copolymer," both of which are incorporated herein by reference in their entirety. The rolled sheet 1306 can finally be scrunched or compressed about its longitudinal axis, as shown at FIG. 13C, to form the slip resistant material 1210. In addition, in various embodiments, a slip resistant material 1210 can also be manufactured by helically wrapping a sheet of compliant material 1302 over a mandrel and/or sliding a tube comprising such a material 1302 over an elongate member.

Referring now to FIG. 14, an endoprosthesis delivery system 1400 is shown. The delivery system 1400 can comprise, in various embodiments, an elongate member 102 is contained within a concentric elongate member 1504 such as an introducer sheath, an endoprosthesis 104, a covering member 106, an end cap 1402 adjacent the edge of the endoprosthesis, and optionally, a tapered end cap 1406. The end cap 1402 prevents the covering member from hanging on the endoprosthesis. In various embodiments, the gap or space, if any, between the end cap 1402 and the edge of the endoprosthesis is less than the diameter of a flexible element. More preferably, the gap between the end cap 1402 and the edge of the endoprosthesis when extended along a curve having a radius commonly encountered in the vasculature is less than the diameter of a flexible element. As such, the end cap 1402 can prevent the endoprosthesis from snagging on the edge of the endoprosthesis.

The tapered end cap 1406 increases in diameter in a proximal to distal direction. In various embodiments, as discussed in greater detail below, the tapered end cap 1406 can further comprise one or more raised surface features on the widest or largest diameter portion of the tapered end cap 1406. These raised surface features can frictionally engage with the inner edge of the concentric elongate member 1504 so that the elongate member 1504 can slide through, but upon advance and contact with the end cap 1406, an increased pull on the elongate member can allow the tapered end cap 1406 through the concentric elongate member 1504. For example, the raised surface features can be a deformable material to facilitate passage through concentric elongate member 1504.

In various embodiments, the end cap 1402, when located on a curved section of vasculature, can optionally bend and elongate along the outer radius. For example, some bending can be facilitated by the end cap 1402 that is constructed of a low durometer tubular piece, as described herein. In other embodiments, the end cap 1402 can comprise a longitudinally compressed polymeric material having creases and folds and abutting the edge of the endoprosthesis and optionally partially deforming thereto, similar to that illustrated in FIG. 12B. The creases and folds provide some stored length that can be stretched when on a curve.

In other embodiments, the end cap 1402 can comprise a small inflatable member that presses against the edge of the endoprosthesis. In other embodiments, the end cap 1402 can comprise an open or closed cell polymeric foam material that presses against the edge of the endoprosthesis, the foam comprising a pre-manufactured component or being formed in place.

As described herein, the endoprosthesis 104 can have a distal edge as well as a proximal edge. As shown, the distal edge can abut or be disposed adjacent to the end cap 1402. Similarly, as shown, the proximal edge can abut or be disposed adjacent to the tapered end cap 1406. Further, as shown, the diameter of the constrained endoprosthesis 104 can be substantially the same as the diameter of the end cap 1402 and/or the diameter of the distal portion of the tapered member 1406.

With particular regard to the compositions of the end cap 1402 and optionally the tapered end cap 1406, the components can comprise all or in part, any of a variety of materials. For instance, both components can comprise a mildly or moderately deformable material, i.e., a low durometer material at least on the section closest to the endoprosthesis. For example, the low durometer material can have a durometer between 15 and 70 Shore on the Type A scale. In various embodiments, the end cap 1402 can be constructed so as to more compliant along the axis parallel to the longitudinal axis of the elongate member than across its radial dimension.

In various embodiments, the end cap 1402 can be at least partially deformed to the edge profile of the endoprosthesis 104. This can be accomplished by way of any suitable process and in any manner that is suitable for the purpose. For instance, the proximal edge of the end cap 1402 can be pressed against the distal end of the endoprosthesis 104, and the deformable properties of the end cap 1402 (or at least the proximal end thereof), can permit the end cap 1402 to at least partially deform to the edge of endoprosthesis 104. In addition or alternatively, in various embodiments, the end cap 1402 can comprise a concave proximal end, so that the thinnest section of the end cap has the largest diameter. Having a thinner section can facilitate improved deformation to the edge profile.

With further regard to the end cap 1402, at its distal end, the end cap 1402 can optionally be coupled to a catheter olive 108. The end cap 1402 can be coupled to the olive 108 in any suitable manner. For example, the distal end of the end cap 1402 can fit into a receiving portion formed in the proximal end of the olive 108 and/or bonded within the receiving portion in any suitable fashion, including any number of suitable techniques and/or using any of the materials described herein (e.g., heat bonding, radio frequency bonding, pressure bonding, glue or adhesives, and the like).

The covering member 106 can extend over at least a portion of the end cap 1402 and beyond the end cap 1402. Likewise, in various embodiments, the covering member 106 can extend over at least a portion of the tapered end cap 1406.

During deployment, the covering member 106 can be removed (e.g. unraveled) to uncover or release the endoprosthesis 104 from a constrained diameter. As this process occurs, the end cap 1402 can prevent the covering member 106 from becoming caught, snagged, or entangled with the edge of the endoprosthesis 104. Rather, the end cap 1402 guides the covering member 106 over the edge of the endoprosthesis 104. The same process can occur at the proximal end of the endoprosthesis 104, except that the covering member 106 can follow the tapered end cap 1406 over the proximal end of the endoprosthesis 104. (Optionally, the end cap 1402 can be a mirror image of the tapered end cap 1406; i.e., its tapered end increases in diameter from a distal to proximal direction.)

In various embodiments, a post-deployment state can take place after and/or in response to deployment of the endoprosthesis 104. A post-deployment state is illustrated at FIG. 15. As shown, the endoprosthesis 104 has been deployed, exposing the elongate member 102. The elongate member 102 can be coupled to the end cap 1402 and the tapered end cap 1406 through a channel formed within each component. The tapered end cap 1406 can be slideable along the elongate member 102 and have a distal face that is substantially the same cross-sectional area and shape as the proximal face of the end cap 1402.

To remove the delivery system 1400 from the body lumen of a patient, a physician can withdraw, or cause to be withdrawn, the elongate member 102. As this occurs, the elongate member 102 can retract proximally through the introducer sheath or other concentric elongate member 1504. The tapered end cap 1406, which is slideable along the elongate member 102 and has a distal cross-sectional area substantially equal to or slightly more than the inner diameter of the introducer sheath 1504, can remain in place against an open end 1502 of the introducer sheath 1504 as the elongate member 102 continues to be withdrawn. Thus, as the elongate member 102 is withdrawn, the proximal face of the end cap 1402 can approach the distal end of the tapered end cap 1406 until contact is made. As contact is made, the end cap 1402, which is frictionally engaged or otherwise secured to the elongate member 102 can act as a backstop to the tapered end cap 1406, and, at this juncture, with an additional pull force applied by the operator, the tapered end cap 1406 can be pulled through the open end 1502 of the concentric elongate member 1504. The tapered end cap 1406 can thus facilitate retraction of the end cap 1402 (which can have a substantially non-tapered proximal face) into the open end 1502 of the outer shaft of the concentric elongate member 1504. Absent the tapered end cap 1406, the end cap 1402 might hang on the open end 1502 as an attempt is made to retract the elongate member 102 back through the concentric elongate member 1504, particularly if the open end 1502 is located on a curve in the vasculature and the elongate member 102 is entering the open end 1502 at an angle relative to the tangential axis at the open end 1502.

Figure 16:
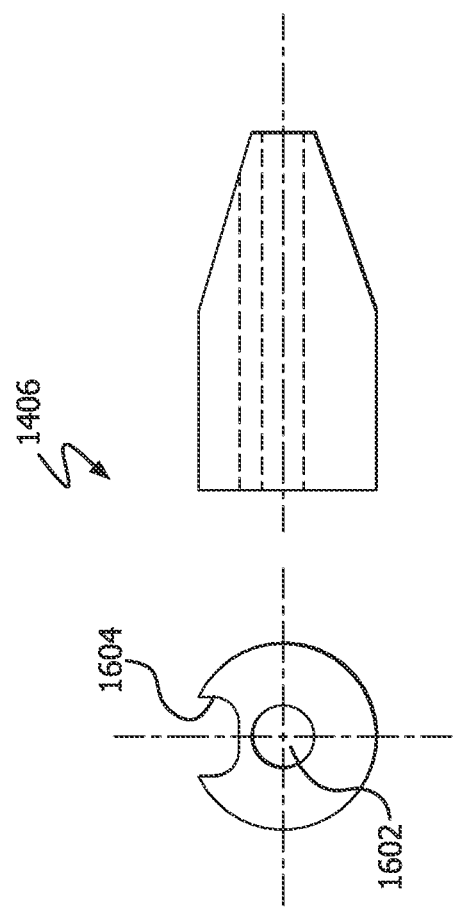
FIG. 16 illustrates a cross-sectional view of a tapered end cap.

With continuing attention to the tapered end cap 1406, and with brief reference to FIG. 16, a channel 1602 is shown formed within the end cap 1406. This channel can accommodate, as discussed above, the inner shaft 102. In addition, a concavity or depression 1604 is shown, which can accommodate a pull line for reduced profile and it is contemplated that a plurality of depressions or other features can exist predicated on system needs.

Figure 17:
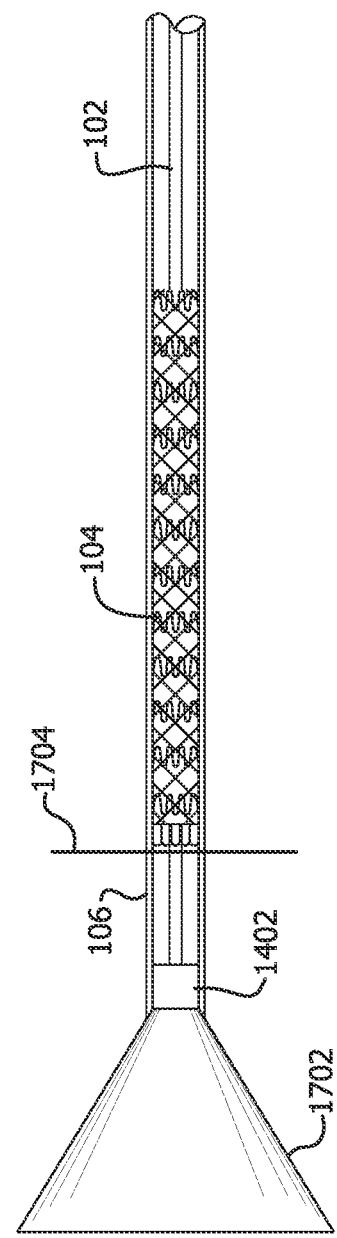
FIG. 17 illustrates a process for loading an endoprosthesis on an inner shaft of an elongate member and within a covering member.

With reference to FIG. 17, in various embodiments, the endoprosthesis 104 can be loaded with the end cap 1402 and the covering member 106 using a loading funnel 1702. In particular, the endoprosthesis 104 can be reduced from an unconstrained diameter to a constrained diameter by feeding the endoprosthesis 104 through the loading funnel 1702. The constrained endoprosthesis 104 can be received, at the reduced diameter portion of the loading funnel 1702, by the covering member 106. An inner elongate member 102 can extend substantially coaxially through the covering member 106, and as the endoprosthetic device 104 is fed through the funnel 1702 into the covering member 106, the endoprosthesis 104 can further substantially coaxially straddle the inner elongate member 102.

Having received the endoprosthesis 104, the covering member 106 can be cut or otherwise severed at a particular location. The location can be along a cutline 1704, and the cutline 1704 can be, as shown, substantially adjacent to, but slightly distal of, the distal end of the endoprosthesis 104. However, care should be taken not to sever the inner elongate member 102 during this process. Further, although a particular cutline 1704 is shown, in various embodiments, the covering member 106 can be severed at any location along the length of the endoprosthesis 104 and/or at any location(s) distal and/or proximal of the endoprosthesis 104. Having established the cutline 1704, any excess covering member 106 can be removed.

In the absence of the excised covering member 106, the end cap 1402 can be coupled to the exposed elongate member. More particularly, the end cap 1402 can, in various embodiments, be mounted on the elongate member and advanced along the elongate member until the end cap 1402 abuts or is compressed against the distal or proximal edge (e.g., the distal apices) of the endoprosthesis 104. The end cap 1402 can be coupled to the elongate member in any manner suitable for this purpose, such as by way of any of the techniques and/or materials described herein. For example, the end cap 1402 can be frictionally engaged to the elongate member, or be glued or otherwise adhesively fixed to the elongate member. Further, the end cap 1402 can be heat bonded, radio frequency bonded, pressured fitted or bonded, and the like to the elongate member 102.

The tapered end cap 1406 can be similarly coupled to the elongate member 102. For instance, the covering member 106 can be removed or excised from a portion of the elongate member 102 proximal to the endoprosthesis 104 and the tapered end cap 1406 mounted on the elongate member 102 by way of the channel 1602 formed in the member 106. The tapered end cap 1406 can be advanced along the elongate member 102 until the tapered end cap 1406 abuts or is compressed against the proximal end of the endoprosthesis 104. The tapered end cap 1406, however, may not be coupled to the elongate member 102, because, as described above, the tapered end cap 1406 can be slideably coupled to the elongate member 102.

In various embodiments, the features and advantages associated with each of the endoprosthesis delivery systems 100, 1200, and 1400, as described above, can be combined in any desirable manner. For example, although the system 100 is not described above as inclusive of a tapered end cap 1406, the system 100 can, in various embodiments, include such a tapered end cap 1406. Similarly, although the compressible material 402 is not described, with respect to system 100 as being folded or ribbed, as disclosed with respect to system 1200, the compressible material 402 can nevertheless comprise such a texture and/or conformation.

A graft comprising any of the grafts and/or stent-grafts described above may be made up of any material which is suitable for use as a graft in the chosen body lumen. A graft may comprise one or a variety of materials. Furthermore, a graft may comprise multiple layers of material, which can be the same material or different material. Although a graft may have several layers of material, the graft may have a layer that is formed into a tube (innermost tube) and an outermost layer that is formed into a tube (outermost tube). In some embodiments, a graft may be fenestrated with a fenestration tool.

Many graft materials are known, and in various embodiments, these materials can be used in combination and assembled together to comprise a graft. These materials may be further extruded, coated and/or formed from wrapped films, and/or a combination thereof. Polymeric materials, biodegradable materials, and/or natural materials can be used for specific applications.

In various embodiments, a graft may comprise synthetic polymers including nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends, and copolymers. In a variety of embodiments, a graft may be made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes. Further, in a variety of embodiments, a graft may comprise expanded fluorocarbon polymers (especially PTFE) materials.

In various embodiments, fluoropolymers, generally referred to herein, may include polytetrafluoroethylene (PTFE), expanded PTFE (ePTFE), fluorinated ethylene propylene (FEP), copolymers of tetrafluoroethylene (TFE) and perfluoro (propyl vinyl ether) (PEA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinylfluoride (PVF). In various embodiments, a graft can comprise any combination of the materials listed above. Further, in various embodiments, a graft may be substantially impermeable and/or permeable to bodily fluids. A substantially impermeable graft may be made from materials that are substantially impermeable to bodily fluids or can be constructed from permeable materials treated or manufactured to be substantially impermeable to bodily fluids (e.g. by layering different types of materials described above or known in the art). In various embodiments, a stent-graft and/or a side-branch stent-graft, as described above, may be made from any combination of the materials described above, including ePTFE.

Any stent, including stent and/or stent members may be generally cylindrical when restrained and/or when unrestrained and may comprise helically arranged undulations having a plurality of helical turns or wraps. In a variety of embodiments, undulations may be aligned so that they are "in-phase" with each other. More specifically, undulations may comprise apices in opposing first and second directions. When these undulations are in-phase, apices in adjacent helical turns are aligned so that apices can be displaced into respective apices of a corresponding undulation in an adjacent helical turn. In certain embodiments, undulations may have a sinusoidal shape, a U shape, a V shape, and/or an ovaloid shape.

In various embodiments, a stent may be fabricated from a variety of biocompatible materials including commonly known materials (or combinations of materials) used in the manufacture of implantable medical devices. Such materials may include 316L stainless steel, cobalt-chromium-nickel-molybdenum-iron alloy ("cobalt-chromium"), other cobalt alloys such as L605, tantalum, nitinol, polymers, biodegradable alloys or polymers, or other biocompatible metals. In some embodiments, any stent and/or stent-graft described herein may comprise a balloon expandable stent and/or stent-graft and/or a self-expanding stent and/or stent-graft. Further, in certain embodiments, a stent may comprise a wire wound stent, which may or may not comprise undulations.

Example 1—Delivery System Construction

In various embodiments, an endoprosthesis delivery system 100 can be manufactured and/or constructed as follows. Generally, an inner shaft 102 wrapping procedure can be followed by an endoprosthesis loading procedure. The inner shaft 102 wrapping procedure can begin with the insertion of a processing mandrel and/or an appropriate inner shaft 102 within a pair of processing chucks coupled to a film wrapping device. The wrapping device can comprise a film payoff head, which can be configured to travel along a length of the inner shaft 102 to wrap a tape or other compressible or compliant material, as described herein, about the shaft 102. Thus, the inner shaft 102 can be wrapped with a compliant material by the wrapping device. In various embodiments, the film payoff head can make a first pass along an axial length of the shaft 102 and a second pass, in the reverse direction, along the shaft 102 as well. However, the film payoff head can, in other embodiments, make as many or as few passes over the shaft 102 as are desired.

One or more flexible elements 110a-110h can, in addition and as described herein, be coupled to the inner shaft 102. More particularly, in various embodiments, one or more flexible elements 110a-110h can be attached or adhered, in any suitable configuration, to the shaft 102 (e.g., over the layer of compliant material deposited, as discussed, above) and/or one or more runs or layers of film or other suitable compliant material layered over each element 110a-110h to bind the elements 110a-110h to the shaft 102. Thus, the inner shaft wrapping procedure can result in a shaft coupled to one or more elements 110a-110h and/or one or more layers of compliant material.

An endoprosthesis 104 can, as part of an endoprosthesis loading procedure, be further loaded on a shaft 102. The shaft 102 can, in various embodiments, be coupled to the one or more flexible elements 110a-110h prior to the loading procedure. Therefore, to load the endoprosthesis onto the shaft 102, an unconstrained endoprosthesis 104 can be inserted over the shaft 102 and fed, in this configuration, into a loading funnel. In addition, as the endoprosthesis 104 enters the loading funnel, each of the flexible elements 1410a-110h can be threaded, as described herein, through one or more of the apices of the endoprosthesis 104. The loading funnel can, in this manner, reduce the endoprosthesis 104 to a constrained diameter about the shaft 102. A covering member 106, as described herein, can be further positioned at the smaller diameter end of the loading funnel, and the constrained endoprosthesis 104 can be thus fed into the covering member 106 at the output of the funnel.

Example 2—Delivery System Construction

Continuing, in various embodiments, an endoprosthesis delivery system can be constructed and/or manufactured with an end cap 1402 and/or a tapered end cap 1406 as follows. An endoprosthesis 104 can, as described herein, be loaded through a loading funnel. A process for loading an endoprosthesis through a loading funnel is also generally described by U.S. Pat. No. 6,702,845 to Cully et al., issued Mar. 9, 2004, entitled "Compacted implantable medical devices and method of compacting such devices" which is hereby incorporated by reference in its entirety. The endoprosthesis 104 can be loaded by insertion through the loading funnel on the inner shaft 102. The distal end of the endoprosthesis can pass through the funnel last, so that the proximal end of the endoprosthesis 104 is received, at the smaller diameter end of the funnel, and as described above, by the covering member 106.

At the distal end of the endoprosthesis 104, the end cap 1402 can be coupled to the distal edge of the shaft 102. For example, in various embodiments, the end cap 1402 can comprise any compliant, compressible, elastomeric materials, and the like, such as Shore A 45 durometer PEBAX, and having an inside diameter sized to fit slightly to the distal edge of the shaft by way of compression, interference, or impression between the shaft 102 and the end cap 1402. The outside diameter of the end cap 1402 can have, in various embodiments, a diameter slightly smaller than a diameter of the loading funnel. Thus, the end cap 1402 can be coupled through the loading funnel to the distal edge of the shaft 102. The end cap 1402 can be pressed against the distal edge to minimize any gap between the end cap 1402 and the distal edge of the shaft. Further, as discussed above, the endoprosthesis 104 can be advanced through the loading funnel and into a constrained configuration within the covering member 106. The end cap 1402 can be bonded to the distal edge of the shaft 102 by any suitable means, including, for example, using an adhesive and/or a melt bonding technique.

In like fashion, the tapered end cap 1406 can be coupled to the proximal edge of the shaft 202. For example, the tapered end cap 1406 can comprise any suitable material, including compliant, compressible, elastomeric materials and the like. More particularly, in various embodiments, the end cap 1406 can comprise a Shore A 40 durometer PEBAX. Further, in various embodiments, a radiopaque marker can be located in an end and/or proximate to an edge of the end cap 1406. The inside diameter of the end cap 1406 can, as discussed herein, be slidably coupled to the shaft 102, and prior to deployment, the tapered end cap 1406 can be positioned near the distal edge of the shaft 102.

Example 3—Delivery System Construction

In various embodiments, a small tubular extrusion of PEBAX can be obtained. The extrusion dimensions can be approximately 1 mm ID×1.2 mm OD, and the material can have a Shore A hardness of 55. A stainless steel mandrel can be inserted into the extrusion lumen and gripped at both ends in a fixture to allow rotation of the extrusion. Further, an ePTFE film, as disclosed by U.S. Pat. No. 5,814,405 to BRANCA, et al., issued Sep. 29, 1998, entitled "Strong, air permeable membranes of polytetrafluoroethylene," which is hereby incorporated by reference in its entirety, can be wrapped about the extruded tube and attached to the extrusion through thermal treatment, for example using a Weller soldering iron. A strip of film (e.g., in various embodiments, a strip of approximately 80 mm in width) can be longitudinally wrapped about the extrusion parallel to the central axis of the extrusion, using minimal tension, by rotating the extrusion. Where such a strip is used, the 80 mm width can be approximately 20 mm longer than the length of the medical implant (e.g., the endoprosthesis 104) being delivered; therefore, once the implant is centrally loaded on this compressible member, there will be approximately 10 mm of compressible material exposed at either end of the implant. In various embodiments, differing numbers of film layers can be applied. For instance, in certain embodiments, approximately 30 layers of film can be applied, thus building up a lofty, compressible zone over which to load an endoprosthesis 104. In various embodiments, the compressible member can be formed in place using an appropriate mold and moldable material such as an injectable foam.

The film strip can then be cut and its loose end attached to an underlying layer, again through the use of localized heat. This compressible zone can then be used as is to load a stent, stent graft, or other endoprosthesis 104. During the loading process, the endoprosthesis 104 can be radially compressed into its delivery dimensions. During compression, the device compresses into the loft of the compressible member, which increases device to catheter retention quality, which ultimately improves accuracy of deployment in the clinical setting. The constraining device can also receive benefit since it too can compress into the compressible material which extends approximately 10 mm at each end of the implant. This can assist in stabilizing it during subsequent delivery and deployment. Optionally, and to add increased benefit, the compressible material can have a layer of silicone (available from NuSil, Carpinteria, Calif. as product #MED 1137) applied to it. Application can be accomplished by dipping, spraying or brushing or the like. Upon curing, this thin, tacky layer adds additional utility in that it can assist in adhering the layers of the ePTFE film together and can provide a tacky surface to which both endoprosthesis 104 and covering member 106 can temporarily grip during the delivery and deployment sequence.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. An endoprosthesis delivery system comprising:
   an elongate member;
   a tubular endoprosthesis comprising a distal edge and being disposed about the elongate member;
   an end cap having a distal end and a proximal end, and being positioned such that the proximal end of the end cap is adjacent to the distal edge of the endoprosthesis;
   a covering member comprising a plurality of fibers at least partially covering and constraining the endoprosthesis to a delivery diameter, and the covering member extending over at least a portion of the end cap and being removable during a deployment of the constrained endoprosthesis; and
   a material surrounding at least a portion of the elongate member, the material being radially compressible in a z-axis, the z-axis being defined through a thickness of the material, the material being collocated with the tubular endoprosthesis at the distal edge of the tubular endoprosthesis, wherein at least one fiber of the plurality of fibers compresses and is partially embedded into the material when constraining the tubular endoprosthesis.

2. The endoprosthesis delivery system of claim 1, wherein the end cap is adapted to prevent the covering member from catching on the distal edge of the endoprosthesis as the covering member is removed.

3. The delivery system of claim 2, wherein the covering member is a sheath that translates relative to the elongate member as covering member is retracted during the deployment of the constrained endoprosthesis.

4. The delivery system of claim 2, wherein the covering member comprises a plurality of fibers.

5. The delivery system of claim 4, wherein the covering member is configured to unravel to facilitate deployment of the constrained endoprosthesis.

6. The delivery system of claim 1, wherein a diameter of the end cap and the delivery diameter of the constrained endoprosthesis are substantially the same.

7. The delivery system of claim 1, wherein the distal end of the end cap is tapered such that the end cap has a smaller diameter than the proximal end of the end cap.

8. The delivery system of claim 1, further comprising a flexible element disposed over the edge of the endoprosthesis.

9. The delivery system of claim 1, further comprising a second end cap having a distal end and a proximal end, and being positioned such that the distal end of the second end cap is positioned adjacent to a proximal edge of the endoprosthesis.

10. The delivery system of claim 9, wherein the second end cap is adapted to translate relative to the end cap.

11. The endoprosthesis delivery system of claim 1, wherein the end cap further includes a raised surface feature operable to frictionally engage an adjacent structure.

12. The endoprosthesis delivery system of claim 1, wherein the end cap is formed of a compliant material.

13. The endoprosthesis delivery system of claim 12, wherein the end cap is more compliant along an axis parallel to a longitudinal axis of the elongate member than across a radial dimension of the end cap.

14. The endoprosthesis delivery system of claim 1, further comprising a flexible element having a proximal end, the covering member having a distal edge positioned at a location proximal the proximal end of the flexible element.

15. The endoprosthesis delivery system of claim 14, wherein a gap between the end cap and the distal edge of the tubular endoprosthesis is less than a diameter of the flexible element.

16. The endoprosthesis delivery system of claim 1, wherein the material is configured to density when compressed.

17. An endoprosthesis delivery system comprising:
- an elongate member;
- a tubular endoprosthesis comprising a distal edge and being disposed about the elongate member;
- an end cap having a distal end and a proximal end, and being positioned such that the proximal end of the end cap is adjacent to the distal edge of the endoprosthesis;
- a covering member at least partially covering and constraining the endoprosthesis to a delivery diameter, and the covering member extending over at least a portion of the end cap and being removable during a deployment of the constrained endoprosthesis;
- a material surrounding at least a portion of the elongate member, the material being radially compressible in a z-axis, the z-axis being defined through a thickness of the material, the material being collocated with the tubular endoprosthesis at the distal edge of the tubular endoprosthesis; and
- a flexible element having a proximal end, the covering member having a distal edge positioned at a location proximal the proximal end of the flexible element;
- wherein a gap between the end cap and the distal edge of the tubular endoprosthesis is less than a diameter of the flexible element.

* * * * *